United States Patent [19]

Helting

[11] 4,007,265
[45] Feb. 1, 1977

[54] METHOD FOR TREATING TETANUS TOXIN WITH A PROTEINASE TO PRODUCE AN ATOXIC IMMUNOGENIC PRODUCT

[75] Inventor: Torsten Bertil Helting, Marbach near Marburg an der Lahn, Germany

[73] Assignee: Behringwerke Aktiengesellschaft, Marburg an der Lahn, Germany

[22] Filed: Oct. 31, 1974

[21] Appl. No.: 519,762

[30] Foreign Application Priority Data

Nov. 3, 1973 Germany .......................... 2355094

[52] U.S. Cl. ..................................... 424/92; 195/4; 195/29

[51] Int. Cl.² ...................... A61K 39/02; C12B 1/00

[58] Field of Search .................... 195/4, 29; 424/92

[56] References Cited

UNITED STATES PATENTS 3,542,920 11/1970 Schwick et al. ..................... 424/92

*Primary Examiner*—Sam Rosen

*Attorney, Agent, or Firm*—Curtis, Morris & Safford

[57] ABSTRACT

An atoxic, immunogenic product obtained by treating tetanus toxin with a proteinase, a process for its manufacture and a tetanus vaccine containing as the essential ingredient said atoxic immunogenic product.

13 Claims, No Drawings

METHOD FOR TREATING TETANUS TOXIN WITH A PROTEINASE TO PRODUCE AN ATOXIC IMMUNOGENIC PRODUCT

The present invention relates to an atoxic, immunogenic product which can be obtained from tetanus toxin with the aid of a proteinase.

The invention furthermore relates to a tetanus vaccine and to a process for preparing it.

It is known that tetanus toxin is highly toxic to mammals and that for using it as immunizing agent it must be rendered non-toxic. It is known to render tetanus toxin non-toxic by treating it with formaldehyde.

Such a tetanus toxin rendered non-toxic, the so-called tetanus toxoid, has the disadvantage that when used as vaccine it may cause vaccination reactions. Therefore, the attempt has been made to inactivate the tetanus toxin and to split the tetanus toxoid obtained with pepsin in another process stage. This process, however, is very time-consuming, because the inactivation requires several weeks.

Now, we have found that an atoxic, immunogenic product can be obtained from tetanus toxin, which when used as a vaccine does not cause vaccination reactions or causes at least much slighter vaccination reactions, by treating the toxin with a proteinase. The reaction product can be worked up in known manner into a vaccine, if desired with the use of an adjuvant.

As proteinases according to the invention, there may be used all protein-splitting enzymes, in particular, however, the enzymes known in scientific literature under the name peptide-peptido-hydrolases. Papain, trypsin and the bacterial proteinases from B. subtilis have proved to be especially suitable. Some microorganisms, for example Streptomyces griseus, are known to produce proteinase mixtures, for example the so-called pronase, which are likewise suitable for the process of the invention.

In the treatment of the tetanus toxin with a proteinase care must be taken that the reaction is carried out in a medium which does not lead to an irreversible denaturation of the protein body tetanus toxin. For this reason, the reactions are carried out in a weakly acidic, neutral to weakly alkaline pH-range, i.e., at a pH-value between 5 and 10.

Under these circumstances, the treatment of the tetanus toxin with the proteinase is effected under the conditions known to an expert as being those under which the enzyme used develops its best activity or at least a sufficiently good activity.

If, for example, papain is used as proteinase, it is advisable to use 0.5 to 2 U, preferably 1 U, of papain per 1 mg of tetanus toxin. The reaction temperature is in this case 40° – 60° C, preferably 53° – 55° C, the pH-value is 5 to 8, preferably 6.5, and the reaction time of the proteinase is several hours, advantageously 1 to 10 hours. It has proved particularly advantageous to carry out the papain treatment in the presence of a compound containing one or several sulfhydryl groups, for example cysteine-hydrochloride.

It trypsin is used, 10 – 1000, preferably 50 – 200, units per mg of tetanus toxin are employed and the incubation is carried out at a temperature of 30° – 50° C, preferably 40° C to 45° C, in a neutral to weakly alkaline pH-range, preferably at pH 7.5 to 8.5, for 1 to 10 hours, preferably for 5 to 7 hours.

On the other hand, the proteinase mixture from B. subtilis or the pronase are used in a ratio of 0.06 – 6 units, preferably 0.3 – 3, units, per mg of tetanus toxin. Temperature and reaction time correspond approximately to those used with trypsin.

If other proteinases are used, the reaction conditions must be varied in such a manner that in general a good to optimum action of the enzyme is ensured.

As the starting material for carrying out the process of the invention, tetanus toxin is used which is obtained in known manner by cultivation of tetanus baccili and following isolation as culture filtrate. If, desired, it may be pre-purified by conducting the purification in such a manner that the purified toxin is then present as solution in 0.15-molar aqueous sodium chloride. Such a tetanus toxin has a concentration of 2,000 to 3,000 Lf per mg of nitrogen toxin, the term Lf standing for Limes floculationis. This is that quantity of antigen which flocks out 1 International Lf-unit of antiserum.

In order to obtain an immunogenic product which is particularly suitable for the further processing into a vaccine, the pre-purified tetanus-toxin, for example in a 0.15 molar sodium chloride solution, may be mixed with the same or manifold volume of a weakly acidic, neutral or weakly alkaline buffer, preferably having a pH value of between 5 and 8, in which the activity of the proteinase to be used is sufficiently ensured, and substances which are known to be activating for the individual enzyme may be added, for example metal ions, chelate formers, oxidizing or reducing substances and the whole is incubated with the proteinase. If papain is used as proteinase, it is suitable to work in a 0.1-molar phosphate buffer of pH 5 – 8, preferably 6.5, which additionally contains 0.001 M of a complex former such as ethylenediaminetetraacetate (EDTA). As another addition, a sulfhydryl compound, for example cystein-hydrochloride in a concentration of 0.0005 to 0.005, preferably 0.001-molar, may be added to this solution.

The proteinases are available in commerce either in dissolved form or, in part, bound to an insoluble carrier. The activity of papain is determined with the aid of alpha-N-benzoyl-L-arginin-ethyl ester (BAEE). One unit of papain (1 U) hydrolyzes 1 $\mu$mol of BAEE per minute at pH 6.2 and 25° C [Kimmel, J. L. and Smith, E. L., J. Biol. Chem. 207, 515 (1954)].

The activity of trypsin is determined as that of papain with the substrate BAEE. One unit of trypsin is that quantity of enzyme which is required to increase the optical density of the solution, measured at a wave length of 253 nm, by 0.001 per minute, at a pH-value of 8.0 [Schwert, G. W. and Tagenaka, Y., Biochim. Biophys. Acta 16, 570 (1955)].

The proteinases prepared from Streptomyces griseus and B. subtilis are defined with the aid of PUK-units. One PUK-unit is that quantity of enzyme which is required to produce an optical density of the solution of 1.0 at a wave length of 660 nm, 40° C and pH 7.4, determined by the Casein-Folin method [Nomoto, M., Narahashi, Y. and Murakami, M., J. of Biochem. (Japan) 48, 593 (1960)].

One milligram of tetanus toxin corresponds to 320 – 400 Lf-units. The treatment of the tetanus toxin with papain is suitably effected for several hours at an elevated temperature. A pre-treatment at a somewhat lower temperature is particularly advantageous. According to a preferred method of carrying out the process of the invention, the reaction mixture is preincubated for 1 hour at 40° to 45° C, such a pre-incubation is carried out especially with small volumes, and then the reaction mixture is incubated for 1 – 5 hours, preferably for 2 hours, at a temperature of 40° – 60° C, preferably 53° – 55° C.

After cooling and, if papain bound to a carrier has been used, after separation of the papain, for example by centrifugation, the reaction mixture is separated into the individual components by a molecular sieving process. Suitably, a process with molecular sieves is used which have a separating effect for molecular weights between 20 000 and 60 000. Particularly suitable for this purpose are cross-linked dextrans, for example Sephadex$^{(R)}$ G-100 or Sephadex$^{(R)}$ G-200 or Bio-Gel$^{(R)}$ P-100. Preferably, a Sephadex G-100 column having the size of 10 × 100 cm is used. For the elution, the eluting agents usually employed for such purposes, in particular buffer solutions, for example 0.10-molar tris(oxymethyl)amino-methane/hydrochloric acid buffer of pH 8.0 which may contain sodium chloride in a concentration of about 0.1 to 1 mole, are used. During elution, the fractions which show an absorption at 280 nm are collected separately. Four Fractions are formed, of which the second one is the desired product. After concentration of the second fraction, for example by lyophilization, further purification can be achieved by repeated chromatography. Thereby, last residues of toxic substances are removed.

Instead of the repeated chromatography or as additional measure for eliminating last residues of toxic substances, the product may be subjected to a treatment with aldehydes. It is known that protein-chemical separation processes lead in very rare cases to a complete separation of undesired proteinic substances; this is especially true on an industrial scale. In view of the high toxicity of the native tetanus toxin, it must be assumed, therefore, that the toxic components are not completely removed in this way.

In the treatment with aldehydes, the product obtained with the aid of proteinases is treated, prior to or after the chromatography, in a protein concentration of about 1 mg of protein per ml or less in a buffer solution of pH 6.8 – 8.5, preferably pH 7.8, and a molarity of the buffer solution of 0.01 – 0.2 M, with 0.015 – 0.3 M of an aliphatic mono- or di-aldehyde having 1 to 6 carbon atoms, preferably formaldehyde, for 14 days to 18 days at 20° to 37° C.

For a further purification, the product may be subjected to a dialysis for 10 to 20, preferably 15, hours against 0.15-molar sodium chloride and/or sterile filtered. For preparing a vaccine, the product is suitably mixed with an adjuvant, for example aluminum hydroxide. The concentration is adjusted to the desired Lf-value by dilution with 0.15-molar sodium chloride solution. The tetanus vaccine so prepared is well tolerated.

The toxicity of this vaccine was tested on Guinea pigs. 5 Groups of 2 Guinea pigs each were given subcutaneous injections of 0.5 ml of a solution of the product prepared according to the invention, using dilutions of 25, 50, 100, 200 and 400 Lf/ml, respectively. The Guinea pigs which were controlled during 4 days after the injection remained healthy and showed a normal increase in weight.

The efficacy of the product of the invention was tested in protective tests on Guinea pigs. 10 Animals were given each 2 ml of product of the invention with 0.75 Lf/ml. After 4 weeks they were exposed to a challenge injection of 20 dlm of tetanus toxin, dlm meaning the dosis letalis minima. The survival rate of the Guinea pigs was 100 % owing to the immunization with the product of the invention.

The tolerance was tested on Guinea pigs. 5 Guinea pigs were given subcutaneously at three different places of the body 0.1 ml of a tetanus antiserum, which contained 1.0, 0.3 and 0.1 International Units, respectively, per ml of tetanus antitoxin. [1 International Unit (I.U.) of a tetanus antiserum is the quantity which with its potency corresponds to that of 0.03384 mg of the tetanus-antitoxin standard established by the WHO (World Health Organization)(Biological Substances -WHO- Publication Geneva 1972, page 14)]. This antiserum was obtained by immunization of Guinea pigs with a known vaccine. At the same time, each animal was given on three other injection places 0.1 ml of a second tetanus serum which likewise contained 1.0, 0.3 and 0.1 I.U, respectively, per ml of tetanus antitoxin. This second tetanus antiserum had been prepared by immunization of Guinea pigs with the product of the invention. After 2 hours, the animals were given intravenously 1 ml of a conventional tetanus fluid vaccine with 100 Lf/ml to which 0.5% of the dyestuff "Evans Blue" had been admixed. After 30 minutes, the animals were sacrificed and the blue coloration formed by the passive skin anaphylaxis was measured. The antiserum produced with the vaccine of the state of the art showed a distinct anaphylaxis. The antiserum produced with the product of the invention was free from any signs of anaphylaxis.

The new vaccines may be used alone or in combination with other vaccines. For combination, there are suitable in particular diphtheria toxoid, pertussis-immunogen, poliomyelitis viruses and measle viruses.

The following Examples illustrate the invention.

EXAMPLE 1

450,000 Lf of tetanus toxin in 15 ml of 0.15 molar sodium chloride solution (with 2,200 Lf/mg of nitrogen) were diluted with 15 ml of a 0.1-molar phosphate buffer of pH 6.5, which contained 0.001-molar EDTA, combined with 1,500 U of soluble papain in 5 ml of 0.15-molar sodium chloride solution and 3 mg of cystein hydrochloride were added.

After mixing, this batch was kept for 1 hour at 45° C, then for 2 hours at 53° C; after having cooled, it was introduced into a Sephadex G-100 column (10 × 100 cm) and chromatographed with a buffer solution of a 0.1-molar sodium chloride solution, which has been adjusted to pH 8 by means of hydrochloric acid ("tris-hydrochloric acid buffer pH 8") while continuously measuring the absorption in the range of the wave length 280 nm. The fractions which showed an absorption in this range were collected separately. 4 Fractions were formed, the first fraction representing a double peak. The second fraction was subjected to a repeated chromatography under the same conditions and the second fraction resulting therefrom was dialyzed for 15 hours against 0.15-molar sodium chloride, filtered under sterile conditions, the concentration of the product was adjusted to 26 Lf/ml by means of 0.15-molar sodium chloride and mixed with aluminum hydroxide up to a concentration of 0.2 % $Al(OH)_3$.

The yield, referred to Lf-units, was 90%. The specific flocculation activity was determined as being 6,800 Lf/mg of nitrogen. The survival rate of Guinea pigs in the protection test was 100%.

The sedimentation constant of the product was found to be 3 S, measured as 1% solution, as compared to 6.4 S of the starting product and the molecular weight was determined as being about 44,000 ± 10% compared with 140,000 for the starting product.

EXAMPLE 2

15 ml of sterile culture filtrate (100,000 Lf), which had been obtained by cultivation of tetanus bacilli and subsequent isolation, were diluted with 15 ml of a 0,1-molar phosphate buffer of pH 6.5 and which contained 0,001 M EDTA, combined with 300 U of soluble papain in 1 ml of 0.15-molar sodium chloride solution and 3 mg of cystein hydrochloride were added. Incubation and working up were carried out as described in Example 1. The yield, referred to Lf-units, was 50%.

EXAMPLE 3

450,000 Lf of tetanus toxin in 15 ml of a 0,15-molar sodium chloride solution (with 2,200 Lf/mg of nitrogen) were diluted with 15 ml of a 0.1-molar phosphate buffer of pH 6.5, which contained 0,001-molar EDTA, combined with 1,500 U of papain bound to a carrier in 5 ml of 0.15-molar sodium chloride solution and 3 mg of cystein hydrochloride were added.

After incubation as described in Example 1, the carrier-bound papain was removed by centrifugation and the supernatant was worked up as described in Example 1.

The yield and the properties of the product obtained corresponded to those described in Example 1.

EXAMPLE 4

15 ml of tetanus toxin (700 mg of protein) were mixed with 135 ml of 0,1-molar tris-HCl buffer of pH 7.8, containing 0,005 moles of $CaCl_2$, 10 mg of pronase were added and the whole was incubated for 1 hour at 45° C and for 2 hours at 55° C. After removal of the small amount of a precipitate, the reaction mixture was adjusted to pH 6.0, concentrated in an ultrafiltration apparatus and the solution was introduced into a column (5 × 100 cm) of Sephadex$^{(R)}$ G-100 and eluted with 0.1 M tris-acetate buffer of pH 6.0, containing 1 M of NaCl. Isolation of the desired fraction was carried out as described in Example 1.

EXAMPLE 5

30 ml of tetanus toxin (0.5 g of protein) were filled up to a volume of 200 ml by dilution with 0.1 molar tris-HCl buffer of pH 8.0 containing 0.001 M of EDTA. After addition of 10 mg of crystallized trypsin, the solution was kept for 6 hours at 45° C. After adjustment of the pH-value to 6.0, the subsequent chromatography was effected on Sephadex$^{(R)}$ G-100, 5 × 100, with 0.1 molar tris-acetate buffer of pH 6.0, containing 1 M of NaCl, as described in Example 1.

We claim:

1. The method of making an atoxic immunogenic product, adaptable to injection, which consists essentially of treating tetanus toxin with a peptide-peptido-hydrolase at a pH between 5 and 10 and not to cause the irreversible denaturation of the protein body of tetanus toxin.

2. The method as in claim 1 wherein said product is purified by molecular sieve chromatography to isolate that fraction thereof having molecular weights between 20,000 and 60,000.

3. The method as in claim 1 wherein said product is treated, at a protein concentration of about 1 mg or less per ml, with 0.015 to 0.3 mole of an aliphatic mono- or di-aldehyde having 1 to 6 carbon atoms for 14 to 28 days at 20° C. to 37° C. at a pH of 6.0 to 8.5.

4. The method as in claim 3 wherein said aldehyde is formaldehyde.

5. The method as in claim 1 wherein said peptide-peptido-hydrolase is a member selected from the group consisting of papain, trypsin, bacterial proteinase from Bacillus subtilis, or pronase.

6. The method as in claim 1 wherein tetanus toxin is treated with 0.5 to 2 U of papain per milligram of toxin.

7. The method as in claim 1 wherein said tetanus toxin is treated with papain at a temperature of 40° C. to 60° C.

8. The method as in claim 1 wherein said tetanus toxin is treated with papain at a pH of 5 to 8.

9. The method as in claim 1 wherein said tetanus toxin is treated with papain in the presence of a compound containing sulfhydryl groups.

10. An atoxic immunogenic product, adaptable to injection, prepared by the method of claim 1.

11. An atoxic immunogenic product, adaptable to injection, prepared by the method of claim 3.

12. A tetanus vaccine comprising the atoxic immunogenic product of claim 10 as the effective ingredient.

13. A tetanus vaccine comprising the atoxic immunogenic product of claim 11 as the effective ingredient.

* * * * *